(12) United States Patent
Horton et al.

(10) Patent No.: US 7,947,632 B2
(45) Date of Patent: May 24, 2011

(54) GELLED HYDROCARBONS FOR OILFIELD PROCESSES, PHOSPHATE ESTER COMPOUNDS USEFUL IN GELLATION OF HYDROCARBONS AND METHODS FOR PRODUCTION AND USE THEREOF

(75) Inventors: David P. Horton, Calgary (CA); Ioan Ghesner, Calgary (CA)

(73) Assignee: Brine-Add Fluids Ltd., Calgary (CA)

( * ) Notice: Subject to any disclaimer, the term of this patent is extended or adjusted under 35 U.S.C. 154(b) by 0 days.

(21) Appl. No.: 12/940,260

(22) Filed: Nov. 5, 2010

(65) Prior Publication Data

US 2011/0046408 A1    Feb. 24, 2011

Related U.S. Application Data

(62) Division of application No. 12/367,841, filed on Feb. 9, 2009.

(60) Provisional application No. 61/027,342, filed on Feb. 8, 2008, provisional application No. 61/030,040, filed on Feb. 20, 2008.

(51) Int. Cl.
*C09K 8/588* (2006.01)
*C07F 9/08* (2006.01)

(52) U.S. Cl. ........ 507/238; 507/203; 507/235; 507/904; 516/21; 516/24; 516/28; 558/70; 558/87; 558/146

(58) Field of Classification Search .................. 507/238, 507/235, 203, 904; 516/21, 24, 28; 558/70, 558/87, 146
See application file for complete search history.

(56) References Cited

U.S. PATENT DOCUMENTS

| | | | |
|---|---|---|---|
| 4,153,649 A | 5/1979 | Griffin, Jr. | |
| 4,382,066 A * | 5/1983 | Rose | ................ 423/10 |
| 4,622,155 A | 11/1986 | Harris et al. | |
| 5,057,233 A | 10/1991 | Huddleston | |
| 5,190,675 A | 3/1993 | Gross | |
| 6,261,998 B1 | 7/2001 | Amin et al. | |
| 6,511,944 B2 | 1/2003 | Taylor et al. | |
| 7,066,262 B2 | 6/2006 | Funkhouser | |
| 2008/0257556 A1 * | 10/2008 | Kippie et al. | ................ 166/372 |

FOREIGN PATENT DOCUMENTS

| | | |
|---|---|---|
| DE | 4209344 | 9/1993 |
| ES | 2035789 | 4/1993 |

OTHER PUBLICATIONS

H. E. Baumgarten, R. A. Setterquist, J. Am. Chem. Soc. 1957, vol. 79, p. 2605-2608.
P. A. Glaude, H. J. Curran, W. J. Pitz, C. K. Westbrook, Kinetic Study of the Combustion of Phosphorus Containing Species, Article presented at 1999 Fall Meeting of the Western State Section of the Combustion Institute, Irvine, CA, Oct. 25-26, 1999.
Erwin Reidel, Anorganische Chemie, 5th Edition, 2002, pp. 492-495.
Catherine E. Housecroft, Alan G. Sharpe, Inorganic Chemistry, 1st Edition, 2001, 00 341-342.
G.M. Kosolapoff, Preparation of Some Mixed Dialkyl Phosphites, J. Am. Chem. Soc., 1951, vol. 73, p. 4989.

* cited by examiner

*Primary Examiner* — Timothy J. Kugel
(74) *Attorney, Agent, or Firm* — Bennett Jones LLP

(57) ABSTRACT

Phosphate esters useful for gelling hydrocarbons in combination with a metal source are disclosed along with methods of preparation of the phosphate esters. Fouling in oil refinery towers has been attributed due to distillation of impurities present in phosphate esters used to gel hydrocarbons for oil well fracturing. The improved method of preparation of the phosphate ester results in a product that substantially reduces or eliminates volatile phosphorus, which is phosphorus impurities that distill up to 250° C., and increases the high temperature viscosity of the hydrocarbon gels formed using the phosphate esters.

19 Claims, 7 Drawing Sheets

¹H NMR spectrum of Ethyloctylphosphite

GELLED HYDROCARBONS FOR OILFIELD PROCESSES, PHOSPHATE ESTER COMPOUNDS USEFUL IN GELLATION OF HYDROCARBONS AND METHODS FOR PRODUCTION AND USE THEREOF

CROSS REFERENCE TO RELATED APPLICATIONS

This is a divisional application of U.S. application Ser. No. 12/367,841 filed Feb. 9, 2009, which is presently pending. U.S. application Ser. No. 12/367,841 and the present application claim priority under 35 U.S.C. §119(e) to U.S. provisional patent application No. 61/027,342 filed Feb. 8, 2008 and to U.S. provisional patent application No. 61/030,040 filed Feb. 20, 2008.

FIELD

The invention relates to gelled hydrocarbons for oilfield processes, phosphate ester compounds useful in gellation of hydrocarbons and methods for production and use thereof. Phosphate esters of greatest interest herein are interchangeably referred to as dialkyl phosphates, phosphate diesters and dialkyl phosphate esters.

BACKGROUND

It has been long known that certain phosphate esters are useful in generating gelled liquids, particularly gelled hydrocarbons. Gelled hydrocarbons, due to their high viscosity and ability to suspend solids, have found several applications in the field of oil recovery. More commonly they are used in stimulation related processes.

Several patents have been issued based on this concept, see for example U.S. Pat. Nos. 4,153,649, 4,622,155, 5,057,233, 5,190,675, and 6,261,998.

Despite the effectiveness of gelled liquid hydrocarbons in forming fractures in subterranean formations, one particular problem with their use has been described in literature. It has been reported that refineries processing oil produced from formations fractured with gelled liquid hydrocarbons have experienced fouling of the distillation towers. Analysis of the fouling material has revealed a high phosphorus content which has been postulated to originate from a phosphate ester distilling at 230-290° C. In response, several patents have been issued for formulations that are claimed to have low volatile phosphorus contribution in the distillate, see U.S. Pat. Nos. 7,066,262, 6,511,944, and US Applications 20070032387 and 20070173413. It has been speculated in the patent literature that decomposition of phosphate esters to lower molecular weight phosphorus compounds and/or the presence of certain low boiling impurities in the commercial mixture are the sources of volatile phosphorus species. Therefore, the use of less volatile trialkyl phosphate in the manufacturing process of the phosphorus based gelling agent as well as the replacement of phosphate esters with monoalkanephosphonic acid monoesters has been suggested as a method to ameliorate the fouling.

A number of studies on the pyrolysis and combustion of phosphate esters and alkylphosphonate esters have been published, see for example, H. E. Baumgarten, R. A. Setterquist *J. Am. Chem. Soc.* 1957, 79, 2605-2608 and P. A. Glaude, H. J. Curran, W. J. Pitz, C. K. Westbrook *Kinetic Study of the Combustion of Phosphorus Containing Species*, Article presented at 1999 Fall Meeting of the Western State Section of the Combustion Institute, Irvine, Calif., Oct. 25-26, 1999, and the references therein.

At elevated temperatures and in the presence of oxygen both phosphates and phosphonates decompose to $P_2O_5$ (solid) along with CO, $CO_2$, $H_2O$, C and $CH_4$. In the absence of oxygen, $P_2O_5$ along with olefins are produced. $P_2O_5$ is the product of dehydration of $H_3PO_4$, neither of which can be distilled under atmospheric pressure (Erwin Riedel, Anorganishe Chemie, 5th edition, 2002, pp. 492-495 and Ch. E. Housecroft, A. G. Sharpe, *Inorganic Chemistry* first edition, 2001, pp 341-342).

SUMMARY

In accordance with a broad aspect of the present invention, there is provided a method for producing an asymmetric dialkyl phosphate ester, the method comprising: (a) reacting a precursor dialkyl phosphite with a transesterifying agent to obtain a transesterified asymmetric dialkyl phosphite; (b) removing any unreacted transesterifying agent and any unreacted precursor dialkyl phosphite from the transesterified asymmetric dialkyl phosphite; and (c) reacting the transesterified asymmetric dialkyl phosphite to form an asymmetric dialkyl phosphate ester.

In accordance with another broad aspect of the present invention, there is provided an asymmetric dialkyl phosphate ester according to the formula:

[i]

$R^1$ is a straight chained alkyl group having 1 to 4 carbon atoms; and $R^2$ is alkyl group having 6 to 20 carbon atoms or an alkoxyalkyl group, $C_nH_{(2n+1)}O(CH_2CH_2O)_xCH_2CH_2$—, where n is about 6 to 16 and x is about 1 or 2, and wherein any amount of phosphate triester that distils without decomposition at temperatures up to 250° C. (ASTM D86) is maintained below 1% by weight.

In accordance with another broad aspect of the present invention, there is provided a gelled hydrocarbon liquid comprising: a hydrocarbon liquid; 1 to 15 kg/m³ (w/v hydrocarbon liquid) of a gelling agent including an asymmetric dialkyl phosphate ester, wherein any amount of phosphate triester that distils without decomposition at temperatures up to 250° C. is maintained below 1% by weight in the gelling agent, and 0.1 to 7.5 kg/m³ (w/v hydrocarbon liquid) of a polyvalent metal cross linking agent.

In accordance with another broad aspect of the present invention, there is provided a method of treating a subterranean well comprising: providing a hydrocarbon liquid; gelling the hydrocarbon liquid to obtain a gelled hydrocarbon liquid by adding (i) a gelling agent including an asymmetric dialkyl phosphate ester; and (ii) a polyvalent metal cross linking agent, wherein any amount of phosphate triester that distils without decomposition at temperatures up to 250° C. is limited to less than or equal to 10 ppm phosphorus in the gelled hydrocarbon distillate; introducing the gelled hydrocarbon liquid to a subterranean well; and manipulating the gelled hydrocarbon liquid to treat a formation accessed by the subterranean well.

It is to be understood that other aspects of the present invention will become readily apparent to those skilled in the art from the following detailed description, wherein various embodiments of the invention are shown and described by way of illustration. As will be realized, the invention is capable for other and different embodiments and its several details are capable of modification in various other respects, all without departing from the spirit and scope of the present invention. Accordingly the detailed description and examples are to be regarded as illustrative in nature and not as restrictive.

BRIEF DESCRIPTION OF THE DRAWINGS

Referring to the drawings, several aspects of the present invention are illustrated by way of example, and not by way of limitation, in detail in the figures, wherein.

DESCRIPTION OF VARIOUS EMBODIMENTS

The description that follows and the embodiments described therein, are provided by way of illustration of an example, or examples, of particular embodiments of the principles of various aspects of the present invention. These examples are provided for the purposes of explanation, and not of limitation, of those principles and of the invention in its various aspects.

Since the net decomposition product of phosphate esters is phosphoric acid or $P_2O_5$ (solid), we hypothesized that the presence in the commercial phosphate ester mixture of certain phosphorus species that can be distilled without decomposition at temperatures below 250° C. using ASTM D86, or at most below 300° C., are in fact the source of most distillable phosphorus.

A typical phosphate ester mixture used in gelling liquid hydrocarbons is produced commercially by reacting triethylphosphate and $P_2O_5$ at elevated temperatures. This reaction produces a polyphosphate intermediate which is further reacted at elevated temperatures with an alcohol (typically a commercial mixture of n-$C_8$ and n-$C_{10}$ alcohols) to produce a mixture of mono, di and trialkyl phosphate esters. The exact composition of the mixture of products and the relative ratios of the components has not been reported in literature. We hypothesized that besides the desired asymmetric dialkylphosphate some symmetric dialkylphosphate, monoalkylphosphate and trialkylphosphate species might form according to Equation 1.

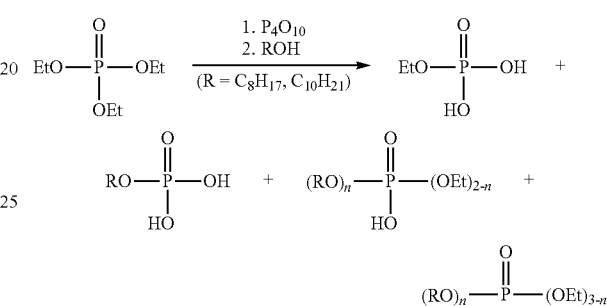

Equation 1

Figure 1:
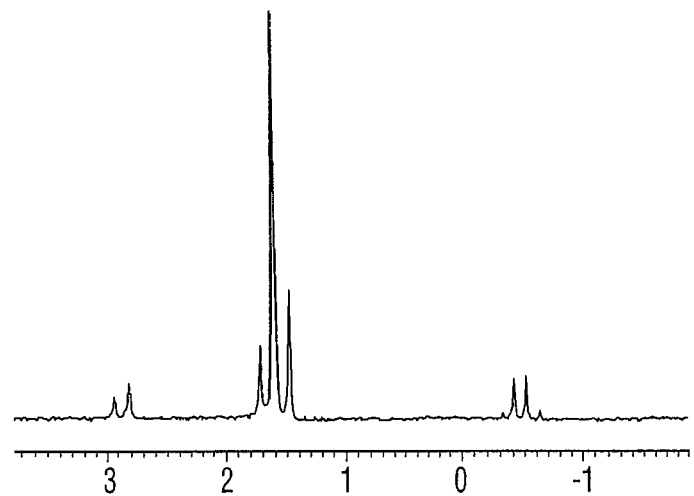
FIG. 1 is a $^{31}$P NMR spectrum of the commercially available phosphorous ester mixture, Rhodafac LO-11A-LA, used in oil based gels (δ −0.63 ppm $(C_2H_5O)_3P(O)$ (0.8%), −0.52 ppm $(R^2O)(C_2H_5O)_2P(O)$ (4.2%), −0.42 ppm $(R^2O)_2(C_2H_5O)P(O)$ (4.3%), −0.32 $(R^2O)_3P(O)$ (0.6%), 1.47 ppm $(C_2H_5O)_2P(O)(OH)$ (16%), 1.67 ppm $(R^2O)(C_2H_5O)P(O)(OH)$ (52.7%), 1.71 ppm $(R^2O)_2P(O)(OH)$ (11.2%), 2.81 ppm $(C_2H_5O)P(O)(OH)_2$ (6.3%), 2.94 ppm $(R^2O)P(O)(OH)_2$ 3.9%), where $R^2=C_8H_{17}$ and $C_{10}H_{21}$).

To study the matter, we acquired NMR spectra for a commercially available gelling agent and some of the components we hypothesized to be present. Indeed, the $^{31}$P{$^1$H} NMR spectrum of a mixed phosphate ester gelling agent, Rhodafac LO-11A-LA, prepared by the reaction described in Equation 1 shows multiple singlet signals which confirms the complex nature of the product mixture (FIG. 1). We independently prepared each assumed component of the mixture and performed NMR measurements on spiked samples. In this manner, we have been able to ascertain that Rhodafac LO-11A-LA consists more or less of 0.8% $(C_2H_5O)_3P(O)$, 4.2% $(R^2O)(C_2H_5O)_2P(O)$, 4.3% $(R^2O)_2(C_2H_5O)P(O)$, 0.6% $(R^2O)_3P(O)$, 16% $(C_2H_5O)_2P(O)(OH)$, 52.7% $(R^2O)(C_2H_5O)P(O)(OH)$, 11.2% $(R^2O)_2P(O)(OH)$, 6.3% $(C_2H_5O)P(O)(OH)_2$, and 3.9% $(R^2O)P(O)(OH)_2$, where $R^2$=n-$C_8H_{17}$ or n-$C_{10}H_{21}$. Each pair of octyl and decyl substituted compounds yield isochronous NMR signals and cannot be distinguished.

Since the phosphate triesters are the species believed to contribute to the majority of distillable phosphorus, a synthetic route to producing an asymmetric dialkyl phosphate ester without coincidental production of the corresponding triesters is desirable.

The present invention provides gelled hydrocarbons, liquid hydrocarbon gelling agents and methods of producing and using liquid hydrocarbon gelling agents and gelled hydrocarbons which may reduce or eliminate their amount of distillable phosphorus content and may increase the high temperature viscosity of the hydrocarbon gels formed.

Thus, in one embodiment, the invention provides an asymmetric dialkyl phosphate ester, which contains, if any, less than 1% by weight of a phosphate triester that distils without decomposition at temperatures up to 250° C. (using the standard ASTM D86). The asymmetric dialkyl phosphate may be represented according to formula [i], which is:

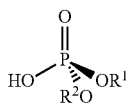

wherein,

R¹ is a straight chained alkyl group having 1 to 4 carbon atoms; and

R² is an alkyl group having 6 to 20 carbon atoms or an alkoxyalkyl group, $C_nH_{(2n+1)}O(CH_2CH_2O)_xCH_2CH_2$—, where n is between about 6 and 16 (inclusive) and x is 1 or 2.

In the definition of R¹ and R², the difference between the two chain lengths should be greater than or equal to about 4 atoms. For example, if R¹ and R² are each alkyl chains, the difference between them is at least 4 atoms. The same is true if R² is an alkoxyalkyl group.

In another embodiment, the invention incorporates a composition of matter that along with the asymmetrical dialkyl phosphate ester includes a monoalkyl phosphate ester and/or a symmetrical dialkyl phosphate ester.

The useful symmetrical dialkyl phosphate ester is a higher molecular weight phosphate diester, for example, having ester substituents greater than C5. These phosphorus compounds tend not to distill without decomposition at temperatures up to 250° C. For example, in one embodiment, a mixture of asymmetric and symmetric dialkyl phosphates may include species of the formulae:

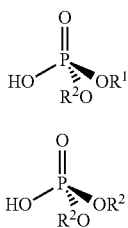

wherein

R¹ is a straight chained alkyl group having 1 to 4 carbon atoms; and

R² is alkyl group having 6 to 20 carbon atoms or an alkoxyalkyl group, $C_nH_{(2n+1)}O(CH_2CH_2O)_xCH_2CH_2$—, where n is about 6 to 16 and x is about 1 or 2.

In the definition of formula [i], the difference between the two chain lengths, R¹ and R², should be greater than or equal to about 4 atoms.

The asymmetric dialkyl phosphate, or the mixture of asymmetric and symmetric dialkyl phosphates, may contain an amount of a monoalkyl phosphate ester. As such a mixture may also be provided including compounds corresponding to the formulae:

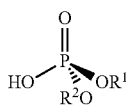

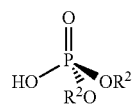

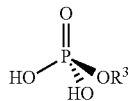

wherein

R¹ is a straight chained alkyl group having 1 to 4 carbon atoms;

R² is alkyl group having 6 to 20 carbon atoms or an alkoxyalkyl group, $C_nH_{(2n+1)}O(CH_2CH_2O)_xCH_2CH_2$—, where n is about 6 to 16 and x is about 1 or 2; and R³ is a straight chain alkyl having 5 to 20 carbon atoms or alkoxyalkyl $C_nH_{(2n+1)}O(CH_2CH_2O)_xCH_2CH_2$—, where n is about 6 to 16 and x is about 1 or 2.

In the definition of formula [i], the difference between the two chain lengths, R¹ and R², should be greater than or equal to about 4 atoms.

It is to be understood that a composition of interest includes the asymmetric dialkyl phosphate ester with or without a monoalkyl phosphate ester and/or a dialkyl phosphate ester. Such compositions may be useful as gelling agents for hydrocarbon liquids. In a gelling agent, it may be useful to control the relative concentrations of the species in order to select for properties such as, for example, cost and gelling properties such as any or all of gelling speed, gel viscosity, gelling duration, resistance to thermal breaking, etc. For example, in one embodiment, a composition may include 50-100% by weight of an asymmetric dialkyl phosphate ester of the formula [i]; 0-50% by weight of a symmetric dialkyl phosphate ester of the formula [ii]; and 0-10% by weight of a monoalkyl phosphate ester of the formula [iii].

In any such gelling agent composition, impurities such as phosphate triesters that distill without decomposition up to 250° C., and possibly up to 300° C., should be limited to less than 1% by weight. If possible, the gelling agent should contain no more than trace amounts, and in one embodiment substantially no, phosphate triesters. If possible, all volatile phosphorus, which generally includes phosphorus impurities that distill without decomposition up to 250° C. or up to 300° C., should be maintained below 1% by weight and if possible kept to no more than trace amounts. Such phosphorus impurities may include, for example, low molecular weight diesters and monoesters, such as phosphate diesters and monoesters with ester substituents having less than five carbon atoms.

As detailed hereinafter, a method is proposed for obtaining reaction products including an asymmetric phosphate diester and, possibly, varying amounts of symmetric phosphate diesters and/or phosphate monoesters substantially without the above-noted impurities. Reaction products having different selected gelling properties can be prepared by reacting specific reactants and/or by varying the molar ratios in which the reactants are reacted.

These phosphate esters may be prepared starting from a dialkyl phosphite and a transesterifying agent. In particular, in one embodiment, a method may include (a) reacting a precursor dialkyl phosphite with a transesterifying agent to obtain a transesterified asymmetric dialkyl phosphite; (b) removing transesterifying agent and any unreacted precursor dialkyl phosphite from the transesterified asymmetric dialkyl phosphite; and (c) reacting the transesterified asymmetric dialkyl phosphite to form an asymmetric dialkyl phosphate ester.

The precursor dialkyl phosphite may be symmetric or asymmetric. Since transesterification becomes more difficult with longer chain moieties, the precursor dialkyl phosphite may be low molecular weight, with straight chain C1 to C4 alkyl groups. In one embodiment, the dialkyl phosphite precursor may be selected from dimethyl, diethyl, dipropyl or dibutyl phosphites. A more readily available phosphite, is diethyl phosphite.

In the reaction, the transesterifying agent acts to replace one or both of the alkyl groups of the dialkyl phosphite precursor. As such, a useful transesterifying agent has a carbon chain backbone that is dissimilar to the alkyl groups of the phosphite precursor. Generally, a transesterifying agent may include a straight chain moiety with a terminal hydroxyl or thiol group. Reasonably, transesterifying agents with terminal hydroxyl groups are most useful. For example, alcohols such as primary alcohol or an ether of an alcohol are useful. In one embodiment, for example, a primary alcohol with a chain length including 6 to 20 carbon atoms and such that the carbon chain length from the alcohol includes at least four more carbon atoms than the largest alkyl moiety of the precursor dialkyl phosphite. In another embodiment, for example, the transesterifying agent may be an ether of an alcohol with the general formula, $C_nH_{(2n+1)}O(CH_2CH_2O)_mH$, where n is about 6 to 16 and m is about 1 to 3. In one embodiment, the transesterifying agent is an n-octanol.

The reaction of dialkyl phosphite and transesterifying agent can be summarized in Equations 2 and 3.

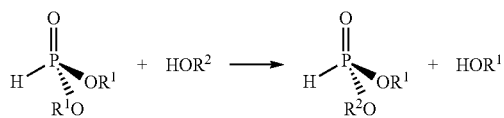

Equation 2

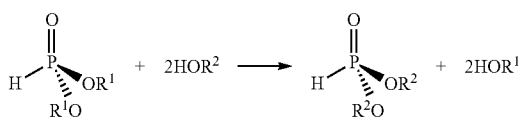

Equation 3

Varying the molar ratios in which the reactants are mixed can lead to products with varying composition and gelling activity. When a dialkyl ($R^1$, $R^1$) phosphite is reacted with an equimolar amount of a dissimilar transesterifying agent, such as alcohol ($HOR^2$), a mixture of asymmetric dialkyl $R^1$, $R^2$ phosphite, symmetric dialkyl $R^2$, $R^2$ phosphite and unreacted symmetric dialkyl $R^1$, $R^1$ phosphite is obtained. The molar ratio between the two products is dependent upon the relative ratio of reactants used.

For example, if diethylphosphite is reacted with an equimolar amount of a dissimilar alcohol, a mixture of asymmetric dialkylphosphite, symmetric dialkylphosphite and unreacted diethyl phosphite is obtained. As a more specific example, if diethylphosphite is reacted with n-octanol in a 1:1 molar ratio ethyloctylphosphite and dioctylphosphite are obtained in a 2.2:1 molar ratio. On the other hand a 50% excess diethylphosphite will increase the product ratio to 3.4:1 and a 100% excess diethylphosphite will give the products in a 4.7:1 ratio.

The transesterification reaction can be carried out in various ways. In one method, for example, the reaction proceeds when reactants are mixed and the temperature is increased above ambient. For most reactants, we have found that the transesterification reaction begins when the reactants are brought to about 100° C. and temperatures that decompose or drive off the reactants should be avoided. Temperatures in the range of 100° C. to 200° C. are believed to be most useful. For example, the reaction of diethylphosphite and n-octanol proceeds at about 150 to 180° C. In another method, catalysis is used and may be carried out at generally ambient temperatures. For example, the transesterification of dialkylphosphites can also be performed catalytically at room temperature in the presence alkali alkoxides, $R^2OM$, where M=Li, Na, K with lithium alkoxides, $R^2OLi$ being a particularly useful catalyst. The catalyst loading required is as low as 1 mol %. Heating is not necessary in such a catalyzed reaction.

After transesterifying, at least some transesterified asymmetric dialkyl phosphite will be obtained along with the by products of transesterification (i.e. $R^1OH$). The mixture generally will also contain amounts of unreacted precursor dialkyl phosphite and unreacted transesterifying agent.

The method proceeds by removing any unreacted transesterifying agent and any unreacted precursor dialkyl phosphite from the transesterified asymmetric dialkyl phosphite. The by products of transesterification may also be removed. The unwanted components can be removed in any one of various ways. For example, distillation and chromatography are two possible processes that may be used to remove the unwanted reactants from the transesterified asymmetric dialkyl phosphite. For large scale processes, where cost controls may be a factor, distillation may be most useful. Using distillation under reduced pressure, the transesterifying agent and unreacted precursor dialkyl phosphite will distill off first leaving a residue of transesterified asymmetric dialkyl phosphite. Any symmetric dialkyl phosphite that is generated from the transesterification reaction (i.e. dialkyl $R^2$, $R^2$ phosphite) will distill after the asymmetric phosphite. As such, if distillation is stopped prior to the distillation of the asymmetric phosphite, the residue will contain the transesterified asymmetric dialkyl phosphite and the transesterified symmetric dialkyl phosphite. If desired, distillation can be continued to separately isolate these two species, although this will increase costs over leaving the residue with a mixture of these species.

Figure 2:
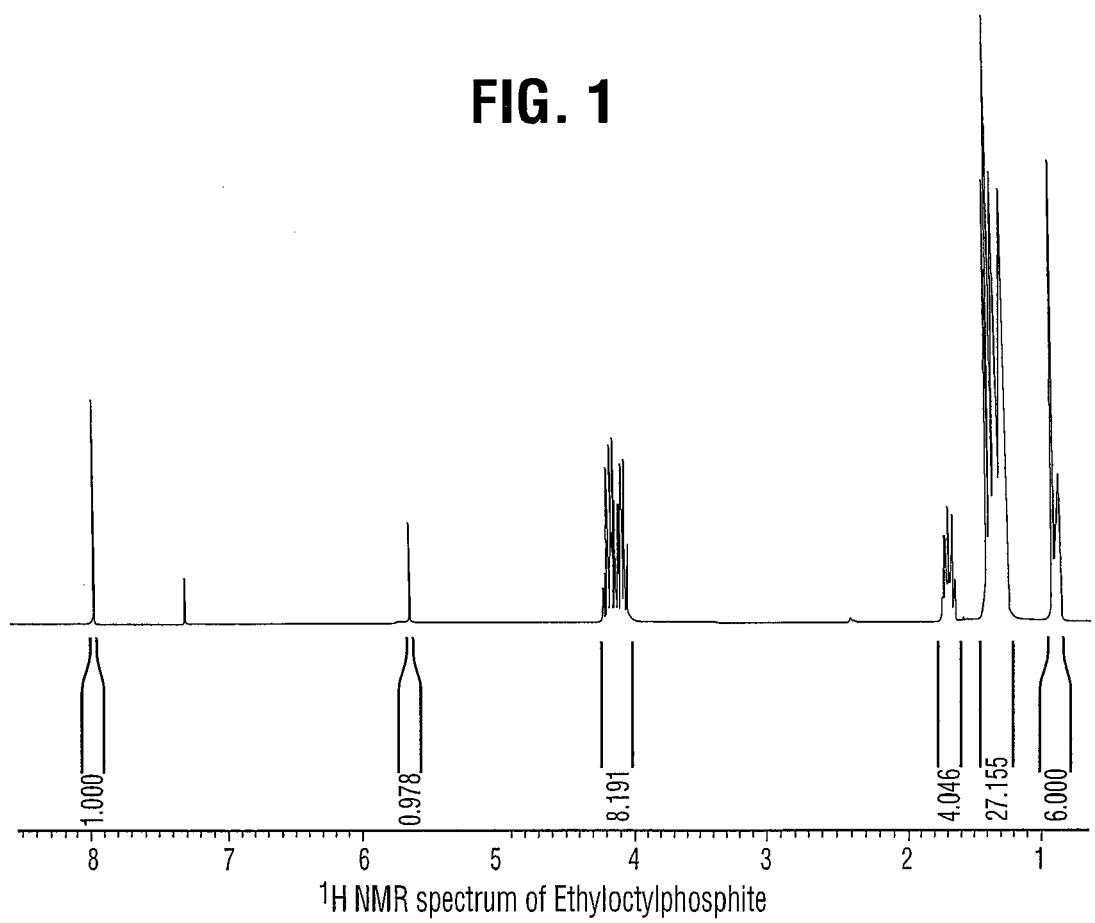
FIG. 2 is a $^1$H NMR spectrum of ethyloctylphosphite.
Figure 3:
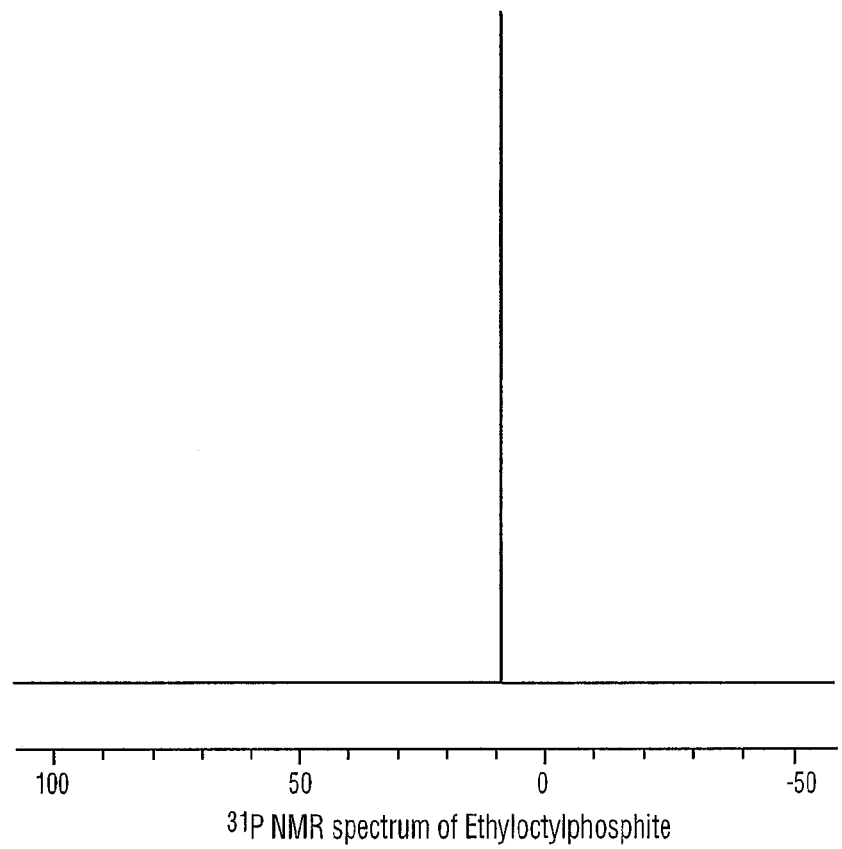
FIG. 3 is a $^{31}$P NMR spectrum of ethyloctylphosphite.

Following the foregoing procedures using diethylphosphite and n-octanol, ethyloctylphosphite (b.p. 110° C., 0.4 torr) can be obtained substantially purely. Likewise, the foregoing procedures using diethylphosphite and n-decanol results in ethyldecylphosphite (b.p. 128° C., 0.3 torr). The $^1H$ and $^{31}P$ NMR spectra of ethyloctylphosphite, $(C_2H_5O)(C_8H_{17}O)P(O)H$, are shown in FIGS. 2 and 3. A characteristic feature which can be observed in the $^1H$ NMR spectrum of all phosphites is the large P-H coupling constant of about 700 Hz.

After the desired phosphite products are separated from the unreacted precursors, the transesterified asymmetric dialkyl phosphite is reacted to form an asymmetric dialkyl phosphate ester. The reaction might generally be considered to be one of oxidation and may be carried out in various ways using, for example, chlorine gas, hypochlorite, or other oxidizing agents such as peroxide. The actual reactions and steps may vary depending on the oxidizing agent used and, for example, may require working the product up as necessary to obtain the final dialkyl phosphate ester.

For example, the reaction using chlorine gas produces a salt intermediate that requires hydrolysis to arrive at the final dialkyl phosphate ester. The reaction with chlorine gas proceeds generally according to Equation 4.

Equation 4

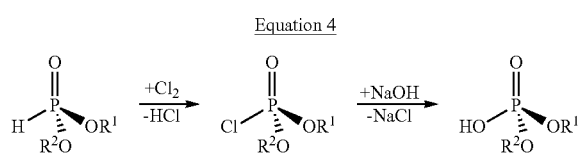

If hypochlorite is used for the conversion, the intermediates may require acidification and neutralization to obtain the final dialkyl phosphate ester.

These reactions may be exothermic. If temperature control is a factor, cooling or controlling the rate of addition of reactants may be useful.

The choice of the reactant used to convert the phosphite intermediates into final products may have an influence on the final product composition. For example, the use of chlorine gas tends to produce only diesters, whereas hypochlorite tends to react a dialkyl phosphite to produce a dialkyl phosphate ester with some amount of monoalkyl phosphate ester also being produced.

Since a product including both an asymmetric dialkyl phosphate ester and with some amount of monoalkyl phosphate ester may be useful, as noted above, a process where an amount of monoalkyl phosphate ester is produced is not problematic. In fact, it may be desirable to add additional monoalkyl phosphate ester to the finally obtained products to arrive at a desired composition. Such additional monoalkyl phosphate ester may be from various sources and need not be generated from the above-noted reaction, as desired.

As has been noted hereinbefore, it is desirable to obtain the asymmetric dialkyl phosphate ester substantially without, or at least with levels below 1% by wt., of any phosphate triesters. The reaction tends not to generate any triesters unless a trialkyl phosphite is present. As such, in one embodiment, the reactants, dialkyl phosphite and transesterifying agent, may be selected to avoid problematic trialkyl phosphite content, which would lead to the eventual generation of triesters. Interestingly, however, it is noted that the step of removing the transesterifying agent from the dialkyl phosphites, such as by distillation, chromatography, etc., may also remove problematic trialkyl phosphites. In particular, in a distillation process under reduced pressure, any trialkyl phosphite is likely to distill off ahead of any transesterified dialkyl phosphite. Other problematic volatile phosphorus compounds (i.e. those phosphorus impurities that distill without decomposition up to 250° C.) that might be generated from the reaction, such as low molecular weight dialkyl phosphate esters (i.e. resulting from unreacted precursor dialkyl phosphites) tend not to be present in the final product, as their precursors may also be removed during the removal step, for example, that including distillation.

An asymmetric dialkyl phosphate ester can be used as a liquid hydrocarbon gelling agent. The asymmetric dialkyl phosphate ester may optionally contain other dialkyl phosphate esters and/or monoalkyl phosphate esters. In use, the asymmetric dialkyl phosphate ester may be combined with a crosslinking agent based on a polyvalent metal salt such as, for example, any one of aluminum (III), iron (III) or iron (II), to form a polyvalent metal salt of the phosphate ester. The liquid hydrocarbons of interest are those useful in wellbore formation and treatment operations. There are many such liquid hydrocarbons including for example, condensates, diesel oil, etc.

To seek to reduce and possibly avoid problems associated with equipment fouling in refineries, phosphorus impurities that distill without decomposition up to 250° C., and possibly up to 300° C., should be substantially avoided in the gelled hydrocarbon or at least maintained low such that distillable phosphorus in the gelled hydrocarbon distillate is less than or equal to 10 ppm or possibly even less than or equal to 6 ppm. The use of asymmetric dialkyl phosphate ester of the present invention as gelling agents, can be useful in achieving such a goal.

A gelled liquid hydrocarbon can be prepared from a liquid hydrocarbon and a polyvalent metal salt of a phosphate ester, and may generally include an amount of water. Optionally, the gelled liquid hydrocarbon also may include any or all of a proppant material, a non emulsifier, a delayed gel breaker effective to break the gelled hydrocarbon fluid over a given period of time, or other components, as desired.

The gelled liquid hydrocarbon, having high viscosity and ability to suspend solids, can be employed in wellbore processes, such as those for oilfield wellbore formation and treatment. For example, the gelled liquid hydrocarbon may be used in as a carrying medium for solids, such as in wellbore stimulation processes such as fracturing or other utilities where liquid hydrocarbons having a viscosity which is greater than their normal viscosity are useful.

In one embodiment, a gelled liquid hydrocarbon according to one or more of the embodiments described above may be provided and introduced into a wellbore to carry out a wellbore process. In one embodiment for example, there is provided a method for stimulating a wellbore including: providing a gelled liquid hydrocarbon and introducing the gelled liquid hydrocarbon to the wellbore. The gelled liquid hydrocarbon may be pumped into the wellbore and may be manipulated to treat the wellbore. In one embodiment, the gelled liquid hydrocarbon may be manipulated, as by pressuring up, to stimulate the wellbore, as by fracturing a formation accessed by the wellbore.

EXAMPLE 1

210.1 g (1.52 mol) of diethylphosphite was heated in the presence of 180 g (1.38 mol) of n-octanol. The mixture was heated while stirring. At 155° C., ethanol began to distil over. The reaction proceeded until 180° C. at which point no further evidence of ethanol production was observed. The resultant mixture was then distilled under vacuum of 0.4 mbar. At 43-48° C., unreacted diethylphosphite was distilled with greater than 99% purity. At 110° C., ethyloctylphosphite was distilled with greater than 99% purity. The remaining residue was determined to be dioctylphosphite with greater than 99% purity. Purity was determined by examination of the NMR spectrum of the materials. The $^1$H NMR of the ethyloctylphosphite produced is shown in FIG. 2, the $^{31}$P NMR is shown in FIG. 3.

The purified ethyloctylphosphite was converted to ethyloctylchlorophosphate by reaction with chlorine and further hydrolyzed to ethyloctylphosphate. To chlorinate the phosphite, chlorine gas was bubbled through pure ethyloctylphosphite while stirring and cooling the solution with an ice water bath. The reaction proceeded to completion, and was indicated by a yellow discolouration of the solution due to the presence of dissolved unreacted chlorine. Subsequently the hydrochloric acid formed was removed under vacuum. Hydrolysis of the resulting chlorophosphates was accomplished by adding 124.8 g of a 25% sodium hydroxide at room temperature. The reaction is summarized in Equation 4.

Figure 4:
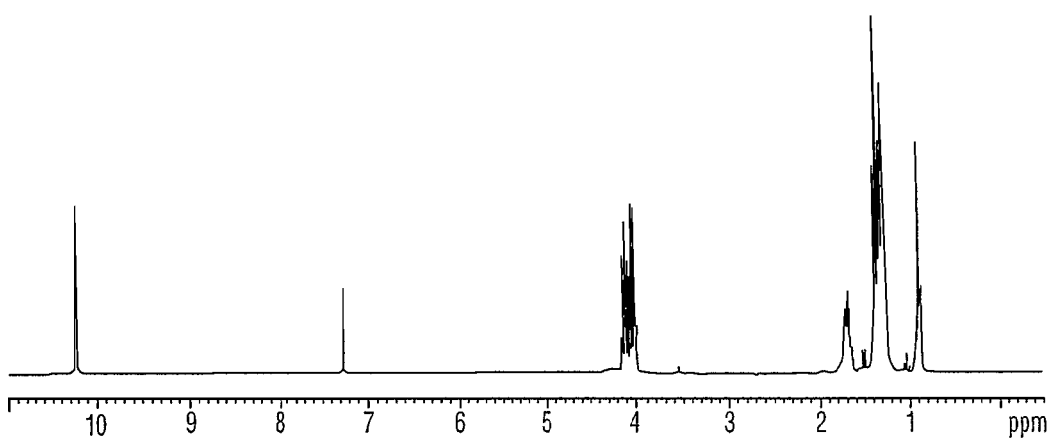
FIG. 4 is a $^1$H NMR spectrum of ethyloctylphosphate.
Figure 5:
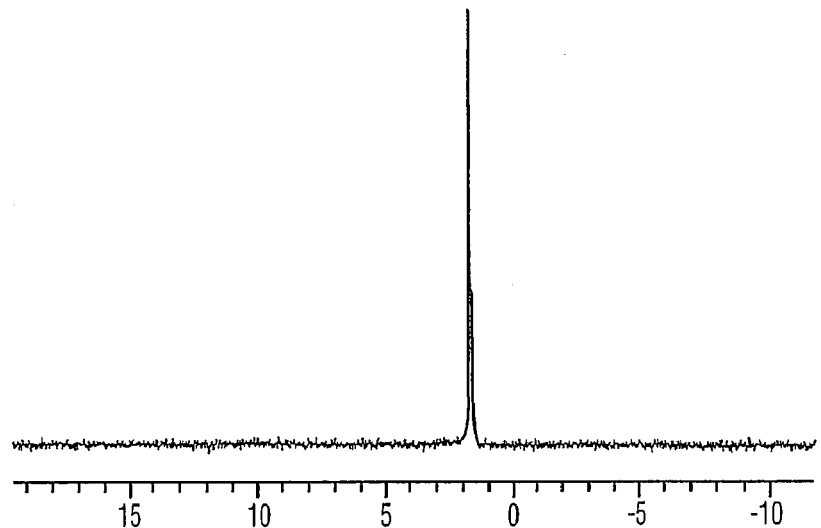
FIG. 5 is a $^{31}$P NMR spectrum of ethyloctylphosphate.

The $^1$H and $^{31}$P NMR spectra of ethyloctylphosphate thus obtained are shown in FIGS. 4 and 5. In the downfield portion of the proton spectrum, the doublet signal due to the P—H group (FIG. 4) has been replaced by a singlet signal due to the P—OH group.

The NMR spectra confirm that the materials produced are substantially pure.

EXAMPLE 2

Figure 6:
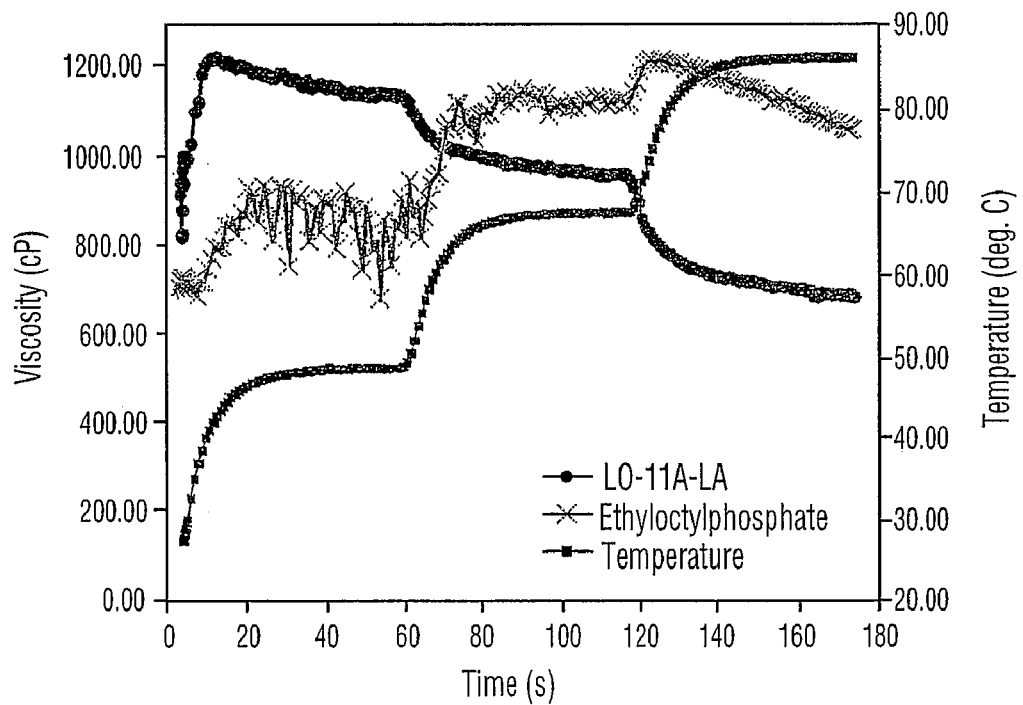
FIG. 6 is a plot of the viscosities of the gels obtained using Rhodafac LO-11A-LA and pure ethyloctylphosphate at various temperatures.

Gellation of diesel using the pure ethyloctylphosphate prepared in Example 1 was examined and compared with gellation using Rhodafac LO-11A-LA. To gel the diesel, 1.2 mL of either Rhodafac LO-11A-LA or ethyloctylphosphate was combined with 1 mL of Brine-Add OG-101C, a commercially available iron sulphate based crosslinker from Brine-Add Fluids Ltd., in 200 mL of diesel while mixing at 1500 rpm, with an overhead mixer. The viscosity profiles of the gels obtained using the pure ethyloctylphosphate and Rhodafac LO-11A-LA were significantly different (FIG. 6). As can be noticed in FIG. 6 the viscosity of the gel obtained using the Rhodafac LO-11A-LA decreases with increasing the temperature. On the other hand the viscosity of the gel obtained using the pure ethyloctylphosphate from Example 1 increases with increasing the temperature.

EXAMPLE 3

Diethylphosphate was synthesized by adding diethylchlorophosphate (65 g; 0.37 mol) to 30.14 g (0.75 mol) sodium hydroxide while stirring and cooling the solution with an ice water bath. The mixture was further acidified by the addition of 18.46 g (0.19 mol) sulphuric acid. The so obtained diethylphosphate was extracted with 100 mL diethyl ether and the volatiles removed under vacuum leaving behind 57 g of product as a colourless liquid.

EXAMPLE 4

Dioctylphosphate was synthesized following a procedure similar to that described in Example 1 for the synthesis of ethyloctylphosphate. The purified dioctylphosphite, obtained as described in Example 1, was converted to dioctylchlorophosphate by reaction with chlorine and further hydrolyzed to dioctylphosphate with a 25% solution of sodium hydroxide at room temperature.

EXAMPLE 5

Octylphosphate was synthesized by the hydrolysis of octyldichlorophosphate, which in turn is obtained in high yield as the reaction product of phosphorus oxychloride, $POCl_3$, and n-octanol. To 180 g (1.17 mol) phosphorus oxychloride was added slowly under stirring 152.4 g (1.17 mol) n-octanol. The mixture was stirred for 2 h at room temperature and the hydrochloric acid removed under vacuum. The so obtained product contains 95% octyldichlorophosphate along with 5% dioctylchlorophosphate. Further purification was achieved by distilling the mixture at 98° C. and 0.4 mbar to give 145 g of pure octyldichlorophosphate as a colourless liquid. The octyldichlorophosphate was hydrolyzed with 150 mL DI water at 50° C. Afterwards the water phase was removed, another 150 mL of DI water were added to the organic phase and the mixture further heated for 4 h at 90° C. Extraction of the product with 100 mL diethyl ether followed by removal of the volatiles gave 121 g of octylphosphate as a viscous colourless liquid.

EXAMPLE 6

Diethyloctylphosphate was prepared from octyldichlorophosphate and sodium ethoxide. To 114 g (0.46 mol) octyl-dichlorophosphate in 100 mL diethyl ether 62.8 g (0.92 mol) sodium ethoxide were added in portions under ice cooling. The mixture was stirred for another hour at room temperature before being hydrolyzed with 200 mL of 1% solution of sodium bicarbonate. The organic phase was recovered and the volatiles removed under reduced pressure leaving behind 120 g of a pale yellow liquid. Further distillation at 129-132° C. and 0.2 mbar gave 81 g of pure product as a colourless liquid.

EXAMPLE 7

Gellation of diesel using diethylphosphate prepared in Example 3 was examined. Gelling of diesel was attempted by adding 1.2 mL diethylphosphate and 1.0 mL of Brine-Add OG-101C, iron sulphate based crosslinker in 200 mL of diesel while mixing at 1500 rpm on an overhead mixer. No gellation of the diesel was noted.

EXAMPLE 8

Gellation of diesel using Dioctylphosphate prepared in Example 4 was examined. Gelling of diesel was attempted by adding 1.2 mL Dioctylphosphate and 0.96 mL of Brine-Add OG-101C, an iron sulphate based crosslinker in 200 mL of Diesel while mixing at 1500 rpm on an overhead mixer. No gellation of the Diesel was noted.

EXAMPLE 9

Gellation of diesel using octylphosphate prepared in Example 4 was examined. Gelling of diesel was attempted by adding 1.2 mL octylphosphate and 0.96 mL of Brine-Add OG-101C, iron sulphate based crosslinker in 200 mL of diesel while mixing at 1500 rpm on an overhead mixer. No gellation of the diesel was noted.

EXAMPLE 10

Diethylphosphate prepared in Example 3 was mixed with ethyloctylphosphate prepared in Example 1 at a ratio of 1:3.5 by weight.

EXAMPLE 11

Dioctylphosphate prepared in Example 4 was mixed with ethyloctylphosphate prepared in Example 1 at ratios of 1:5 by weight.

EXAMPLE 12

Diethyloctylphosphate prepared in Example 6 was mixed with ethyloctylphosphate prepared in Example 1 at ratios of 1:9 by weight.

EXAMPLE 13

Octylphosphate prepared in Example 3 was mixed with ethyloctylphosphate prepared in Example 1 at a ratio of 1:19 and 1:5.66 by weight.

EXAMPLE 14

Figure 7:
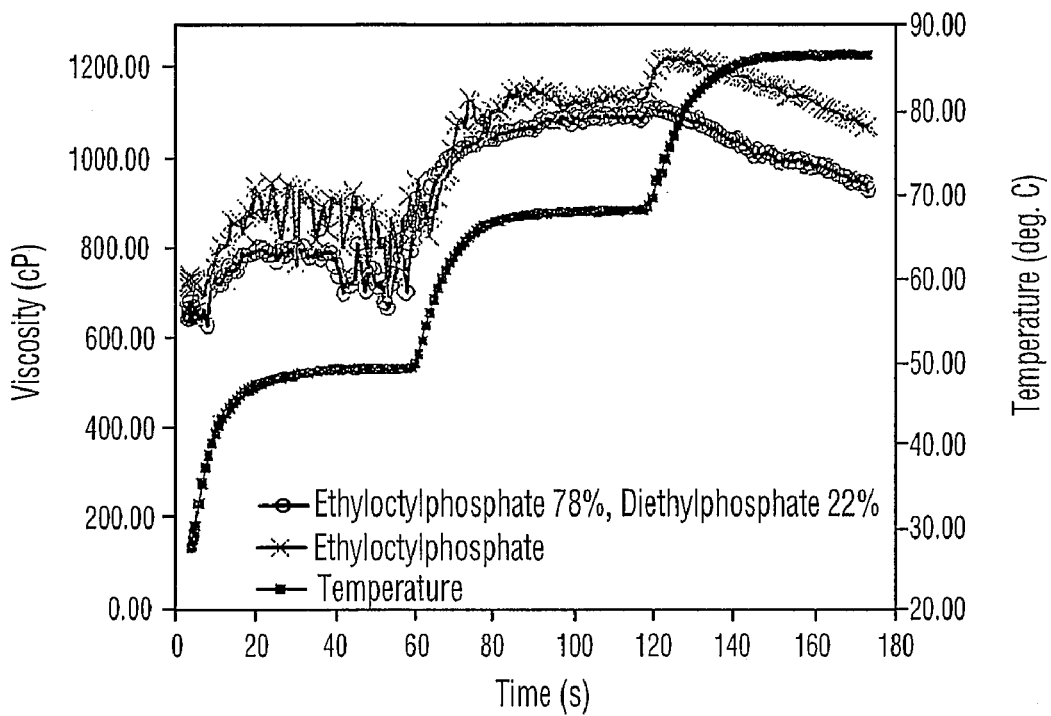
FIG. 7 is a plot of the viscosities of the gels obtained with ethyloctylphosphate and mixture of ethyloctylphosphate and diethyl phosphate.

Gellation of diesel using the mixture prepared in Example 10 was examined. To gel the diesel, 1.2 mL of the mixture from Example 10 was combined with 1.00 mL of Brine-Add OG-101C, an iron sulphate based crosslinker in 200 mL of diesel while mixing at 1500 rpm on an overhead mixer. The viscosity profiles of the gels subsequently obtained are shown in FIG. 7. Addition of diethylphosphate to ethyloctylphosphate slightly decreases the overall viscosities of gels as compared with gels prepared from pure ethyloctylphosphate.

EXAMPLE 15

Figure 8:
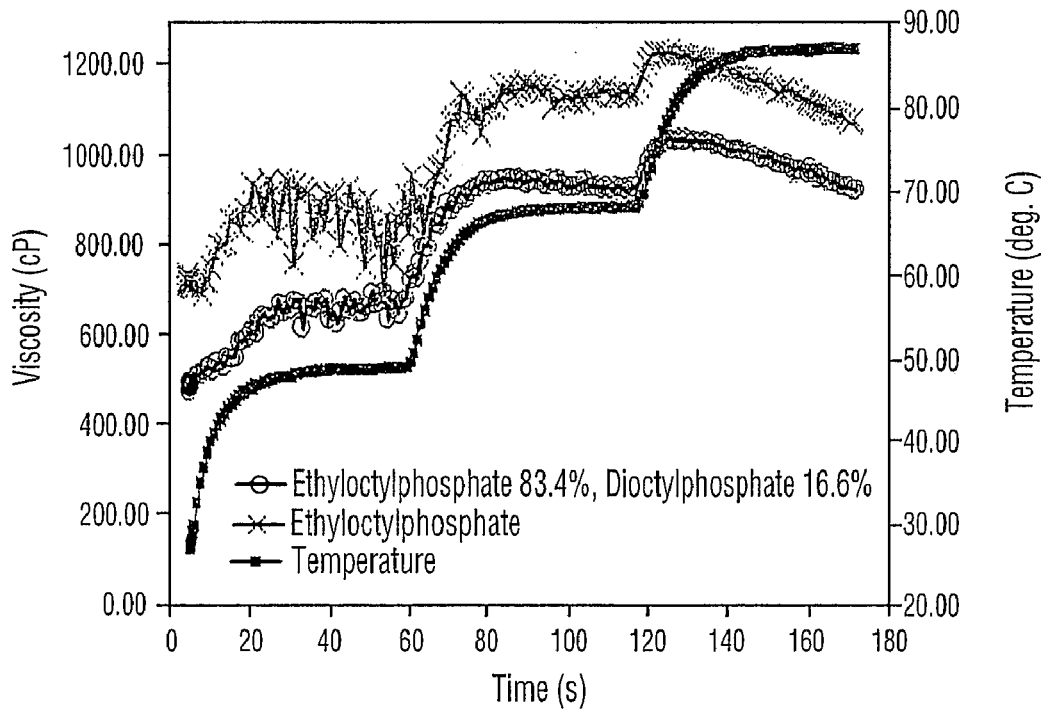
FIG. 8 is a plot of the viscosities of the gels obtained with ethyloctylphosphate and mixture of ethyloctylphosphate and dioctylphosphate.

Gellation of diesel using the mixture prepared in Example 11 was examined. To gel the diesel, 1.2 mL of the mixture from Example 11 was combined with 1.00 mL of Brine-Add OG-101C, an iron sulphate based crosslinker in 200 mL of diesel while mixing at 1500 rpm on a Caframo® overhead mixer. The viscosity profiles of the gels subsequently obtained are shown in FIG. 8. As was observed with the symmetric diethylphosphate in Example 14, the longer alkyl chain, dioctylphosphate, decreases the overall viscosity of the gels as compared with gels prepared from pure ethyloctylphosphate. An increase in the time required for the gel to form was also observed.

EXAMPLE 16

Figure 9:
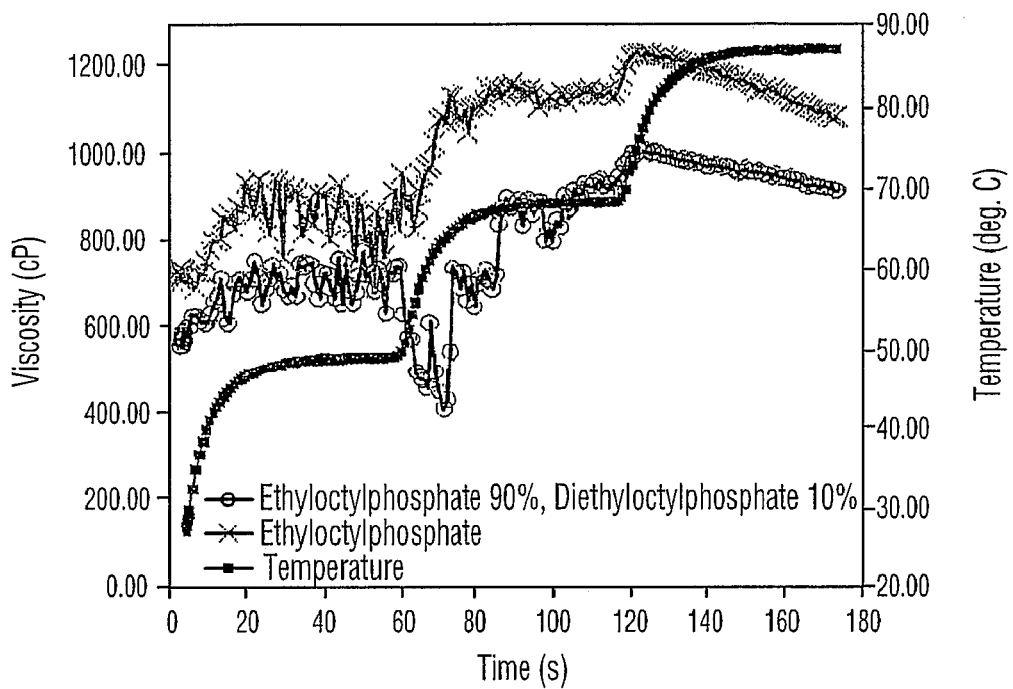
FIG. 9 is a plot of the viscosities of the gels obtained with ethyloctylphosphate and mixture of ethyloctylphosphate and diethyloctylphosphate.

Gellation of diesel using the mixture prepared in Example 12 was examined. To gel the diesel, 1.2 mL of the mixture from Example 12 was combined with 1.00 mL of Brine-Add OG-101C, an iron sulphate based crosslinker in 200 mL of diesel while mixing at 1500 rpm on an overhead mixer. The viscosity profiles of the gels subsequently obtained are shown in FIG. 9. Adding 10% diethyloctylphosphate to pure ethyloctylphosphate decreases the overall viscosity of the gels as compared with gels prepared from pure ethyloctylphosphate (FIG. 9).

EXAMPLE 17

Figure 10:
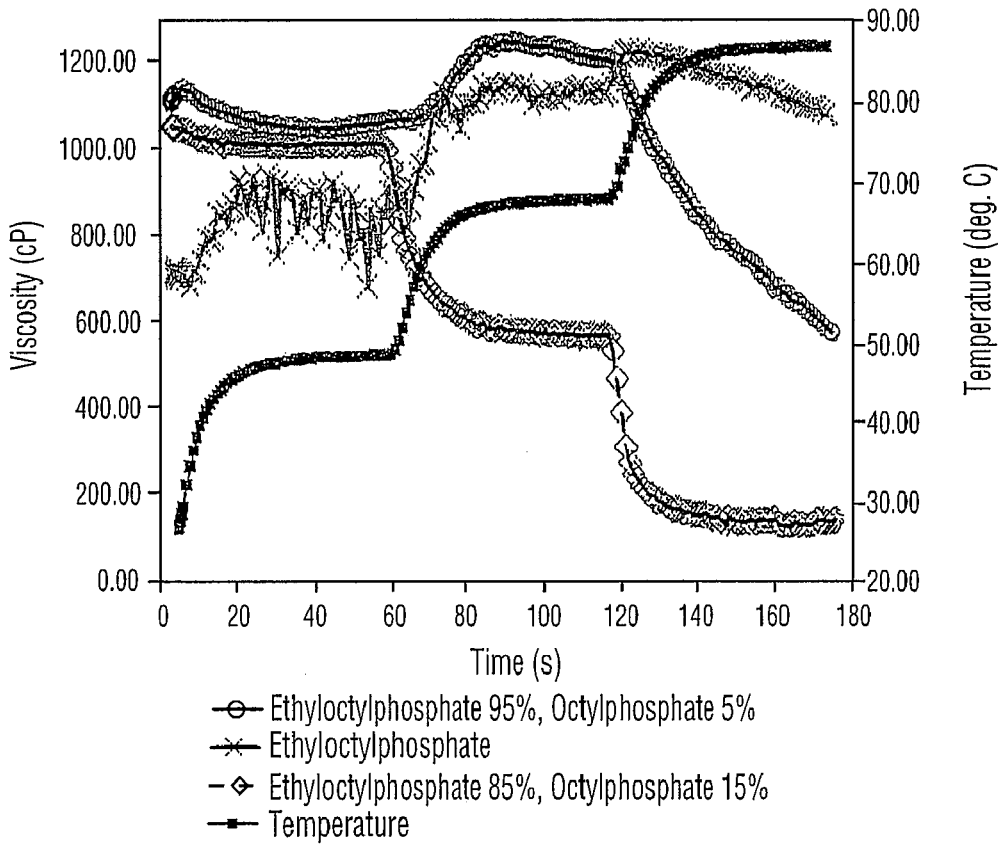
FIG. 10 is a plot of the viscosities of the gels obtained with ethyloctylphosphate and mixtures of ethyloctylphosphate and octylphosphate at two ratios.

Gellation of diesel using the mixtures prepared in Example 13 was examined. To gel the Diesel, 1.2 mL of the respective mixture from Example 13 was combined with 1.0 mL of Brine-Add OG-101C, an iron sulphate based crosslinker in 200 mL of diesel while mixing at 1500 rpm on an overhead mixer. The viscosity profiles of the gels subsequently obtained are shown in FIG. 10.

Surprisingly, adding 5% octylphosphate to ethyloctylphosphate increases the viscosity of the gel as compared with the corresponding gel prepared from ethyloctylphosphate up to a temperature of 70° C. (FIG. 10). A decrease in the time required for the diesel to gel was noticed with the material containing 5% octylphosphate with 95% ethyloctylphosphate. Adding 15% of the octylphosphate has a detrimental effect as the viscosity of the gel is decreased over the entire temperature range. It appeared that concentrations beyond about 10% by weight of octylphosphate in the ethyloctylphosphate failed to provide the beneficial gelling results.

EXAMPLE 18

210.1 g (1.52 mol) diethylphosphite was heated in the presence of 180 g (1.38 mol) n-octanol. The mixture was heated while stirring. At 150° C., ethanol began to distil over. The reaction proceeded until 180° C. at which point no further evidence of ethanol production was observed. The resultant mixture was then distilled under vacuum of 0.6 mbar. At 43-48° C., unreacted diethylphosphite was distilled, leaving behind 252 g of a 1:2.2 mole mixture of ethyloctylphosphite and dioctylphosphite. The mixture of phosphites was converted to the corresponding chlorophosphates by reaction with chlorine and further hydrolyzed to ethyloctylphosphate and dioctylphosphate respectively. To chlorinate the phosphites, chlorine gas was bubbled through the solution of phosphites while stirring and cooling the solution with an ice water bath. The reaction proceeded to completion, and was indicated by the solution turning yellow due to the presence of dissolved unreacted chlorine. Afterwards the hydrochloric acid formed was removed under vacuum. Hydrolysis of the resulting chlorophosphates was accomplished by adding 166 g of a 25% sodium hydroxide at room temperature. 256 g of a colourless liquid consisting of ethyloctylphosphate 69% and dioctylphosphate 31% was obtained.

EXAMPLE 19

252 g of a 1:2.2 mixture of ethyloctylphosphite and dioctylphosphite was prepared as described in Example 20. The phosphites were further converted to the corresponding phosphates by reacting them with sodium hypochlorite. The ethyloctylphosphite and dioctylphosphite mixture was added to 918 g sodium hypochlorite solution (10-13% as active chlorine). The addition was performed dropwise with water cooling (temperature below 30° C.) and the pH maintained between 10-11.5 with 25% NaOH. After all the phosphite was added the pH is raised to about 11-11.5 and the reaction mixture was stirred until the pH stayed above 11. Afterwards the mixture was treated dropwise with sulfuric acid (98%) until a pH of 2 was measured. Two phases formed and the upper yellow organic phase was separated. 265 g of a viscous colourless liquid was obtained, the composition confirmed with $^{31}$P NMR, consisting of 3.6% octylphosphate ($\delta$ 3.5 ppm, singlet), 66.3% ethyloctylphosphate ($\delta$ 1.87 ppm, singlet) and 30.1% dioctylphosphate ($\delta$ 2.1 ppm, singlet).

EXAMPLE 20

50 g (0.38 mol) of n-octanol was premixed with 3.5 mL of a 2.2M methanol solution of lithium methoxide. The mixture was rapidly added at room temperature to 53 g (0.38 mol) diethylphosphite. The colour of the solution changed from colourless to yellow. The resultant mixture was then distilled under vacuum of 1.00 mBar. At 23° C. ethanol was removed. At 43-48° C., unreacted diethyl phosphite was distilled, with the remaining 65 g comprising a 1.6:1 mole mixture of ethyloctylphosphite and dioctylphosphite. The phosphites were further converted to the corresponding phosphates by reacting them with sodium hypochlorite as described in Example 19.

EXAMPLE 21

20 g (0.15 mol) of n-octanol was premixed with 0.29 g sodium tert-butoxide and 0.46 mL tetramethylethylenediamine. The mixture was added rapidly at room temperature to 21.23 g (0.15 mol) diethylphosphite. The resultant mixture was then distilled under vacuum of 1.00 mBar. At 23° C. ethanol was removed. At 43-48° C., unreacted diethylphosphite was distilled, with the remaining 65 g comprising a 1.6:1 mole mixture of ethyloctylphosphite and dioctylphosphite. The phosphites are further converted to the corresponding phosphates by reacting them with sodium hypochlorite as described in Example 19.

EXAMPLE 22

50 g (0.38 mol) of n-octanol was premixed with 3.5 mL of a 2.2M Methanol solution of lithium methoxide. The mixture was rapidly added at room temperature to 53 g (0.38 mol)

diethylphosphite and the colour of the solution was observed to change from colourless to yellow. The ethanol formed during the reaction was removed under vacuum, leaving behind 87.3 g of a mixture of diethylphosphite (13 mole %), ethyloctylphosphite (52 mole %), and dioctylphosphite (35 mole %). The phosphites were further converted to the corresponding phosphates by reacting them with sodium hypochlorite. This was achieved by adding the mixture of phosphites to 343 g sodium hypochlorite solution (10-13% as active chlorine). The addition was performed dropwise with water cooling (temperature below 30° C.) and the pH maintained between 10-11.5 with 25% NaOH. After all the phosphite was added the pH was raised to about 11-11.5 and the reaction mixture was stirred until the pH remained above 11. Subsequently the mixture was treated dropwise with hydrochloric acid until a pH of 2 was measured. 10 g of sodium chloride was also added in order to aid in extraction of diethylphosphate from the water phase. Two phases were observed to form and the upper yellow organic phase was separated. 94 g of a viscous colourless liquid are obtained and the composition determined by $^{31}P$ NMR. The composition consisted of 3.6 mol % octylphosphate (δ 3.5 ppm, singlet), 52.7 mol % ethyloctylphosphate (δ 1.8 ppm, singlet), 17 mol % diethylphosphate (δ 1.6 ppm, singlet), and 26.7 mol % dioctylphosphate (δ 82.1 ppm, singlet).

EXAMPLE 23

50 g of a 3:7 weight ratio of n-hexadecanol:n-octadecanol was premixed with 1.7 mL of a 2.2M Methanol solution of lithium methoxide. The mixture was rapidly added at room temperature to 26.4 g (0.19 mol) diethylphosphite. The resultant mixture was then distilled under vacuum of 1.00 mBar. At 23° C. ethanol was removed. At 43-48° C., unreacted diethylphosphite was distilled in greater than 99% purity, leaving behind 61.5 g of a mixture of ethylhexadecylphosphite, ethyloctadecylphosphite, dihexadecylphosphite, dioctadecylphosphite and hexadecyloctadecylphosphite as a white solid. The resulting phosphites were subsequently converted to the corresponding phosphates by reacting them with sodium hypochlorite. To accomplish this, 50 g of the above mixture was added to 104 g sodium hypochlorite solution (10-13% as active chlorine). The addition was performed in portions at temperatures between 35-40° C. while maintaining the pH between 9-11.5 with 25% NaOH. After all the phosphite was added the pH was raised to about 11-11.5 and the reaction mixture was stirred at 60° C. until the pH remained above 11. Afterwards the mixture was treated dropwise with 98% sulphuric acid until a pH of 2 was measured. The solid product was separated from the water phase by filtration. 51.3 g of a white solid was obtained consisting of ethylhexadecylphosphite, ethyloctadecylphosphate, dihexadecylphosphate, dioctadecylphosphate and hexadecyloctadecylphospate. The ratio between the asymmetric and symmetric phosphates was determined to be 1.9:1 as measured by $^{31}P$ NMR.

EXAMPLE 24

40 g (0.2 mol) of dibutylphosphite was heated while stirring in the presence of 26.8 g (0.2 mol) of n-octanol. At 180° C., butyl alcohol was observed to distil. The reaction proceeded until 200° C. at which point no further evidence of butyl alcohol production was observed. The resultant mixture was then distilled under vacuum of 1.00 mBar. At 92° C., unreacted dibutylphosphite was distilled in greater than 99% purity, leaving behind 42 g of a mixture of butyloctylphosphite and dioctylphosphite. The resulting phosphites were further converted to the corresponding phosphates by reacting them with sodium hypochlorite. To achieve this, 42 g of the mixture of dioctylphosphite and butyloctylphosphite was added to 148 g sodium hypochlorite solution (10-13% as active chlorine). The addition was done dropwise with water cooling while maintaining a temperature between 30-40° C. and maintaining the pH between 9-11.5 using 25% sodium hydroxide. After addition of the phosphite, the pH was raised to about 11-11.5 and the reaction mixture was stirred until the pH remained above 11. Afterwards the mixture is treated dropwise with sulphuric acid (98%) until a pH of 2 was observed. At this point two phases formed and the upper organic phase was separated. 48 g of a viscous colourless liquid was obtained consisting of butyloctylphosphite and dioctylphosphate. In the $^{31}P$ NMR the two dialkylphosphates are isochronous and cannot be distinguished. Hence only one singlet at 2.1 ppm was observed.

EXAMPLE 25

60 g (0.43 mol) diethylphosphite was heated in the presence of 60 g (0.43 mol) ethylene glycol phenyl ether. The mixture was heated while stirring. At 150° C., ethanol was observed to distil. The reaction proceeded until 180° C. at which point no further evidence of ethanol production was observed. The resultant mixture was then distilled under vacuum of 0.6 mbar. At 43-48° C., unreacted diethylphosphite was distilled leaving 252 g of a 1:2.2 mol mixture of ethyl(ethyleneglycolphenlylether)phosphite and di(ethyleneglycolphenlylether)phosphite. The resulting phosphites were further converted to the corresponding phosphates by reacting them with sodium hypochlorite as described in Example 19.

EXAMPLE 26

The reaction of 54 g (0.39 mol) diethylphosphite with 67.5 g (0.35 mol) diethyleneglycol monohexylether, followed by the oxidation of the resulting phosphites with sodium hypochlorite was carried out as in Example 25.

EXAMPLE 27

Figure 11:
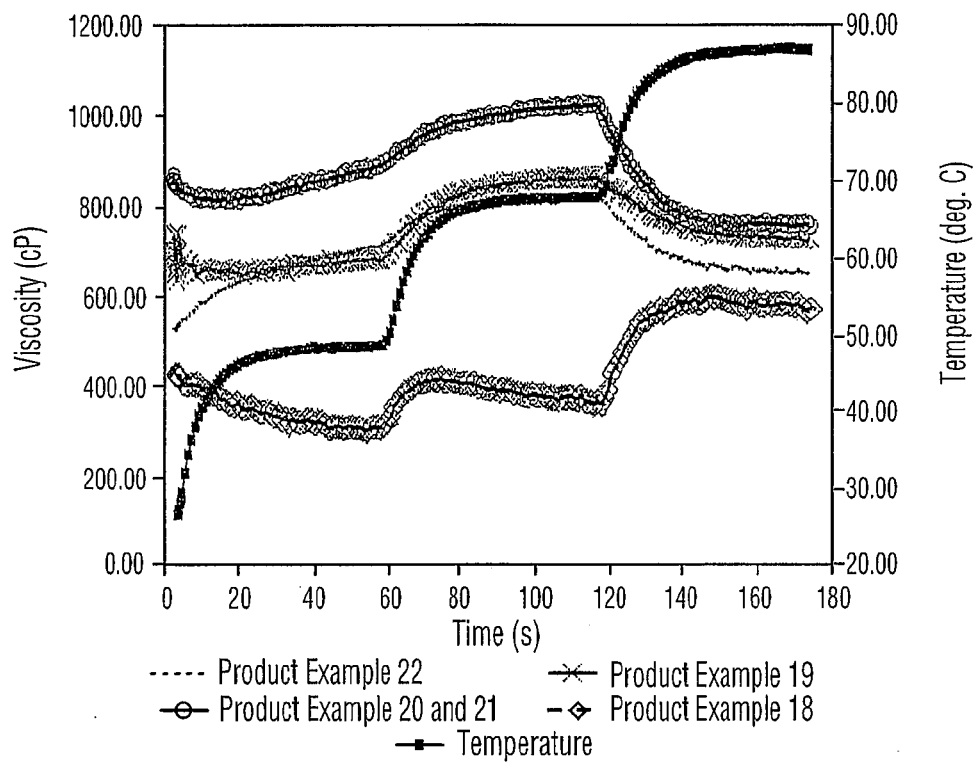
FIG. 11 is a plot of the viscosities of the gels obtained with products from Examples 18 to 22.
Figure 12:
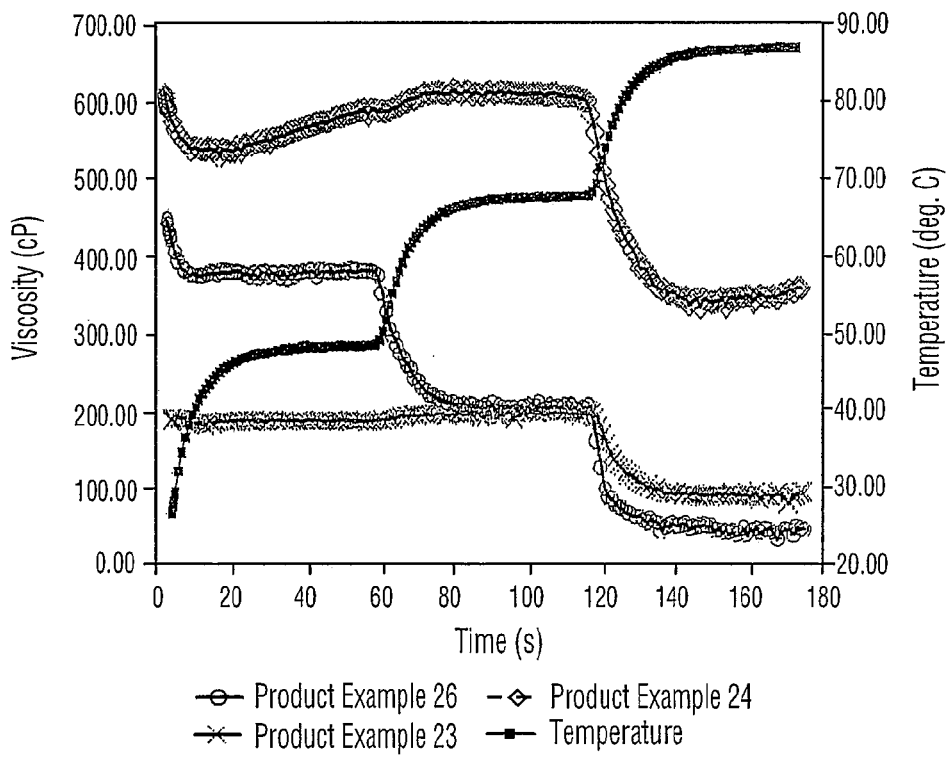
FIG. 12 is a plot of the viscosities of the gels obtained with products from Examples 23, 24 and 26.

Gellation of Diesel using the mixtures prepared in Example 18-26 was examined. To gel the Diesel, 1.2 mL of the respective mixture from Example 18-26 was combined with 1.0 mL of Brine-Add OG-101C, an iron sulphate based crosslinker in 200 mL of diesel while mixing at 1500 rpm on an overhead mixer. With the exception of the product from Example 25 all other materials gelled the diesel. The viscosity profiles of the gels subsequently obtained are shown in FIGS. 11 and 12.

Figure 13:
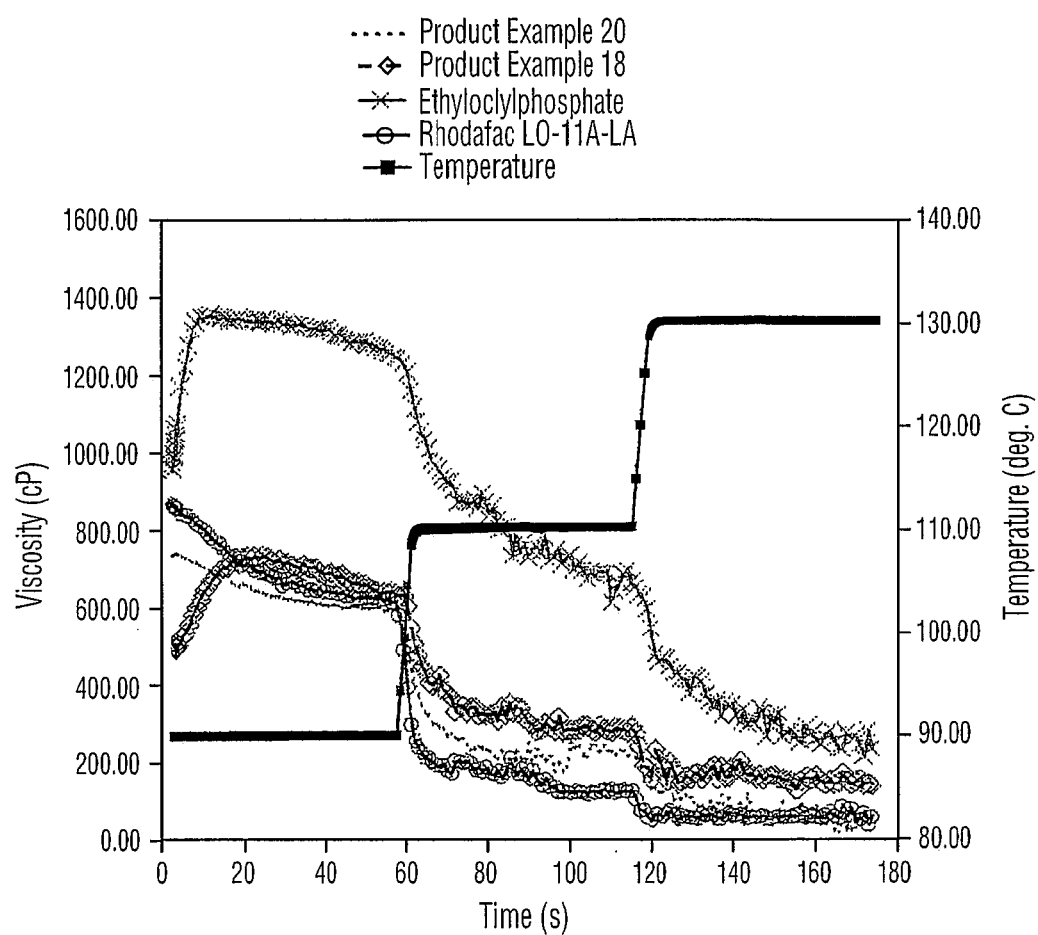
FIG. 13 is a plot of the high temperature viscosities of the gels obtained with Rhodafac LO-11A-LA and products from Examples 1, 18 and 20.

Comparative viscosity measurements in the temperature range 90-130° C. indicate that at high temperatures the gels prepared with products from Example 1, 18, and 20 produce higher viscosity gels than the gels prepared using the commercial product Rhodafac LO-11A-LA (FIG. 13). The general trend indicates that increasing the asymmetric ethyloctylphosphate content of the phosphate ester mixture used to generate oil based gels results in an increase in the thermal stability of the gels.

Conversely, the presence of small amounts of monoester in the phosphate ester mixture will increase the low temperature viscosities of the gels and decrease the high temperature stability of the gels.

EXAMPLE 28

Hydrocarbon gels were prepared using either Rhodafac LO-11A-LA, or one of the phosphate esters produced in Examples 1, 3, 6, 18 or 20. The phosphate esters were added on to a typical fracturing fluid hydrocarbon, C-2000. C-2000 is a commercially available mixture of hydrocarbons which has an initial boiling point of about 110° C. and is 80% distilled at about 250° C. Each phosphate ester sample was added such that the C-2000 contained 950 ppm total phosphorus. A gel was then achieved by adding 2 mL of Brine-Add OG-101C, an iron sulphate based crosslinker, 0.8mL of Brine-Add OG-103B, a slurry of magnesium oxide in mineral oil breaker to 400mL C2000 while mixing at 1500 rpm on an overhead mixer. Samples were then placed in 500 mL cylindrical stainless steel cells and rolled at 80° C. for 16h to simulate a typical fracturing treatment. 100 mL of the resulting fluid was distilled according to ASTM method D86-04b, "Standard Method for Distillation of Petroleum Products at Atmospheric Pressure". The distillation was performed in triplicate for each system and samples collected submitted to a contract laboratory for Phosphorus Analysis by an ICP Analyzer (Inductively Coupled Plasma). The reported detection limit for the method is 0.2 ppm phosphorus. The average phosphorus content in each of base fluids is summarized in Table 1.

TABLE 1

Distillable Phosphorus From Various Phosphate Esters

| Gellant | Volatile Phosphorus (ppm) |
| --- | --- |
| Rhodafac LO-11A-LA | 32.2 |
| Ethyloctylphosphate (Product Example 1) | 0.7 |
| Diethylphosphate (Product Example 3) | 13.9 |
| Diethyloctylphosphate (Product Example 6) | 207.5 |
| Mixed Ethyloctylphosphate:Dioctylphosphate (Product Example 18) | 2.9 |
| Mixed Ethyloctylphosphate:Dioctylphosphate:Octylphosphate (Product Example 20) | 5.7 |

As can be seen in Table 1 the highest phosphorus values 207.5 and 13.9 respectively, were found in the samples containing the triester; diethyloctylphosphate and the diester, diethylphosphate. The samples containing the asymmetric diester, ethyloctyiphosphate, the diester, dioctylphosphate, and the monoester, octylphosphate have the least contribution to distillable phosphorus. The distillable phosphorus values for these samples are in the range 0.7 ppm to 5.7 ppm. The gel prepared from ethyloctyiphosphate contained virtually no distillable phosphorus indicating that this compound does not contribute to distillable phosphorus.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are know or later come to be known to those of ordinary skill in the art are intended to be encompassed by the elements of the claims. Moreover, nothing disclosed herein is intended to be dedicated to the public regardless of whether such disclosure is explicitly recited in the claims. No claim element is to be construed under the provisions of 35 USC 112, sixth paragraph, unless the element is expressly recited using the phrase "means for" or "step for".

We claim:

1. A method for producing an asymmetric dialkyl phosphate ester, the method comprising:
   (a) reacting a precursor dialkyl phosphite with a transesterifying agent to obtain a transesterified asymmetric dialkyl phosphite;
   (b) removing any unreacted transesterifying agent and any unreacted precursor dialkyl phosphite from the transesterified asymmetric dialkyl phosphite; and
   (c) reacting the transesterified asymmetric dialkyl phosphite to form an asymmetric dialkyl phosphate ester.

2. The method of claim 1 wherein the precursor dialkyl phosphite is symmetric.

3. The method of claim 1 wherein the precursor dialkyl phosphite includes a straight chain C1 to C4 alkyl group.

4. The method of claim 1 wherein the precursor dialkyl phosphite is selected from the group consisting of dimethyl phosphite, diethyl phosphite, dipropyl phosphite and dibutyl phosphite.

5. The method of claim 1 wherein the precursor dialkyl phosphite is diethyl phosphite.

6. The method of claim 1 wherein the transesterifying agent includes a carbon chain backbone that is dissimilar to the alkyl groups of the precursor dialkyl phosphite.

7. The method of claim 1 wherein the transesterifying agent is a primary alcohol with a carbon chain length including 6 to 20 atoms and such that the carbon chain length from the primary alcohol includes at least four more carbon atoms than the largest alkyl group of the precursor dialkyl phosphite.

8. The method of claim 1 wherein the transesterifying agent is an ether of an alcohol with a general formula, $C_nH_{(2n+1)}O(CH_2CH_2O)_mH$, where n is about 6 to 16 and m is about 1 to 3 and such that the ether of an alcohol includes a backbone chain length including at least four more atoms than the largest alkyl group of the precursor dialkyl phosphite.

9. The method of claim 1 wherein the transesterifying agent is an n-octanol.

10. The method of claim 1 wherein reacting a precursor dialkyl phosphite with a transesterifying agent also generates a transesterified symmetric dialkyl phosphite.

11. The method of claim 1 wherein removing uses distillation.

12. The method of claim 1 wherein reacting a precursor dialkyl phosphite with a transesterifying agent also generates a transesterified symmetric dialkyl phosphite and removing produces a mixture of the transesterified asymmetric dialkyl phosphite and the transesterified symmetric dialkyl phosphite.

13. The method of claim 1 wherein reacting the transesterified asymmetric dialkyl phosphite to form an asymmetric dialkyl phosphate ester includes oxidation of the transesterified asymmetric dialkyl phosphite.

14. The method of claim 1 further comprising adding an amount of monoalkyl phosphate ester to the asymmetric dialkyl phosphate ester.

15. An asymmetric dialkyl phosphate ester according to the formula:

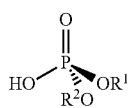 [i]

$R^1$ is a straight chained alkyl group having 1 to 4 carbon atoms; and $R^2$ is alkyl group having 6 to 20 carbon atoms or an alkoxyalkyl group, $C_nH_{(2n+1)}O(CH_2CH_2O)_xCH_2CH_2—$, where n is about 6 to 16 and x is about 1 or 2, and wherein any amount of phosphate triester that distils without decomposition at temperatures up to 250° C. (ASTM D86) is maintained below 1% by weight.

16. The asymmetric dialkyl phosphate ester of claim 15 wherein $R^2$ is a C8 alkyl group.

17. The asymmetric dialkyl phosphate ester of claim 15 wherein $R^1$ is an ethyl group.

18. The asymmetric dialkyl phosphate ester of claim 15 wherein any amount phosphorus impurities that distil without decomposition at temperatures up to 250° C. (ASTM D86) is maintained below 1% by weight.

19. The asymmetric dialkyl phosphate ester of claim 15 wherein $R^2$ has a chain length of about 4 atoms more than the chain length of $R^1$.

* * * * *